(12) United States Patent
Schur et al.

(10) Patent No.: US 9,532,798 B2
(45) Date of Patent: *Jan. 3, 2017

(54) CUTTING WIRE ASSEMBLY FOR USE WITH A CATHETER

(71) Applicants: Israel Schur, Teaneck, NJ (US); Rex Medical, L.P., Conshohocken, PA (US)

(72) Inventors: Israel Schur, Teaneck, NJ (US); James F. McGuckin, Jr., Radnor, PA (US); James Erich Bressler, Langhorne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/738,857

(22) Filed: Jun. 13, 2015

(65) Prior Publication Data
US 2015/0272614 A1   Oct. 1, 2015

Related U.S. Application Data

(60) Continuation of application No. 14/176,128, filed on Feb. 9, 2014, now abandoned, which is a division of application No. 13/226,735, filed on Sep. 7, 2011, now Pat. No. 8,685,050.

(60) Provisional application No. 61/390,217, filed on Oct. 6, 2010.

(51) Int. Cl.
*A61B 17/22*   (2006.01)
*A61B 17/3207*   (2006.01)

(52) U.S. Cl.
CPC .................. *A61B 17/320725* (2013.01); *A61B 2017/22001* (2013.01); *A61B 2017/22061* (2013.01); *A61B 2017/320733* (2013.01)

(58) Field of Classification Search
CPC ...... A61M 25/00; A61M 25/10; A61M 29/00; A61B 17/32; A61B 17/3207; A61B 17/320725; A61B 2017/22001; A61B 2017/22038; A61B 2017/22051
See application file for complete search history.

(56) References Cited

U.S. PATENT DOCUMENTS

| | | | |
|---|---|---|---|
| 5,158,564 A | 10/1992 | Schnepp-pesch |
| 5,176,693 A | 1/1993 | Pannek, Jr. |
| 5,196,024 A | 3/1993 | Barath |

(Continued)

FOREIGN PATENT DOCUMENTS

| | | |
|---|---|---|
| WO | WO-98/19608 | 5/1998 |
| WO | WO-2004/041329 | 5/2004 |

(Continued)

OTHER PUBLICATIONS

EP-11 18 3669—European Search Report. Date of completion of the search, Jan. 23, 2012.

*Primary Examiner* — Ashley Fishback

(57) ABSTRACT

A method of treating a lesion in a body lumen to enlarge a passageway in the lumen including inserting a cutting member and tracking member through a first lumen of a catheter, withdrawing the catheter from the cutting member and tracking member, inserting the catheter over the tracking member and leaving the cutting member outside the catheter, and expanding a portion of the catheter to move the cutting member into cutting contact with the lesion. A device for treating a lesion in a body lumen including a cutting member and tracking member is also provided.

14 Claims, 6 Drawing Sheets

(56) References Cited

U.S. PATENT DOCUMENTS

| | | |
|---|---|---|
| 5,211,651 A | 5/1993 | Reger |
| 5,282,484 A | 2/1994 | Reger |
| 5,320,634 A | 6/1994 | Vigil |
| 5,431,673 A | 7/1995 | Summers |
| 5,527,326 A | 6/1996 | Hermann |
| 5,549,552 A | 8/1996 | Peters et al. |
| 5,554,163 A | 9/1996 | Shturman |
| 5,556,408 A | 9/1996 | Farhat |
| 5,616,149 A | 4/1997 | Barath |
| 5,628,746 A | 5/1997 | Clayman |
| 5,658,301 A | 8/1997 | Lemaitre |
| 5,665,098 A | 9/1997 | Kelly |
| 5,697,944 A | 12/1997 | Lary |
| 5,728,123 A | 3/1998 | Lemelson |
| 5,772,676 A | 6/1998 | Cuschieri |
| 5,797,935 A | 8/1998 | Barath |
| 5,897,567 A | 4/1999 | Ressemann |
| 5,904,679 A | 5/1999 | Clayman |
| 5,941,869 A | 8/1999 | Patterson |
| 6,022,362 A | 2/2000 | Lee |
| 6,027,514 A | 2/2000 | Stine |
| 6,036,708 A | 3/2000 | Sciver |
| 6,156,043 A | 12/2000 | Krahn |
| 6,165,187 A | 12/2000 | Reger |
| 6,165,195 A | 12/2000 | Wilson |
| 6,210,380 B1 | 4/2001 | Mauch |
| 6,221,090 B1 | 4/2001 | Wilson |
| 6,264,667 B1 | 7/2001 | McGuckin, Jr. |
| 6,361,544 B1 | 3/2002 | Wilson |
| 6,387,108 B1 | 5/2002 | Taylor |
| 6,394,995 B1 | 5/2002 | Solar |
| 6,440,147 B1 | 8/2002 | Lee |
| 6,447,501 B1 | 9/2002 | Solar |
| 6,475,222 B1 | 11/2002 | Berg |
| 6,494,875 B1 | 12/2002 | Mauch |
| 6,508,836 B2 | 1/2003 | Wilson |
| 6,565,588 B1 | 5/2003 | Clement |
| 6,632,231 B2 | 10/2003 | Radisch, Jr. |
| 6,702,831 B2 | 3/2004 | Lee |
| 6,740,104 B1 | 5/2004 | Solar |
| 6,746,463 B1 | 6/2004 | Schwartz |
| 6,780,174 B2 | 8/2004 | Mauch |
| 6,780,179 B2 | 8/2004 | Lee |
| 6,780,199 B2 | 8/2004 | Solar |
| 6,796,989 B2 | 9/2004 | Uflacker |
| 6,808,531 B2 | 10/2004 | Lafontaine |
| 6,824,551 B2 | 11/2004 | Trerotola |
| 6,835,059 B2 | 12/2004 | Skinner |
| 6,872,204 B2 | 3/2005 | Houser |
| 6,942,680 B2 | 9/2005 | Grayzel |
| 6,951,566 B2 | 10/2005 | Lary |
| 7,008,434 B2 | 3/2006 | Kurz |
| 7,008,438 B2 | 3/2006 | O'Brien |
| 7,029,450 B2 | 4/2006 | Gellman |
| 7,070,576 B2 | 7/2006 | O'Brien |
| 7,131,981 B2 | 11/2006 | Appling et al. |
| 7,147,631 B2 | 12/2006 | Scopton |
| 7,153,315 B2 | 12/2006 | Miller |
| 7,172,609 B2 | 2/2007 | Radisch, Jr. |
| 7,179,024 B2 | 2/2007 | Greenhalgh |
| 7,252,674 B2 | 8/2007 | Wyzgala |
| 7,270,673 B2 | 9/2007 | Yee |
| 7,279,002 B2 | 10/2007 | Shaw |
| 7,291,158 B2 | 11/2007 | Crow |
| 7,294,117 B2 | 11/2007 | Provost-tine |
| 7,303,572 B2 | 12/2007 | Melsheimer |
| 7,329,267 B2 | 2/2008 | Weber |
| 7,344,546 B2 | 3/2008 | Wulfman |
| 7,396,358 B2 | 7/2008 | Appling |
| 7,399,307 B2 | 7/2008 | Evans |
| 7,416,555 B2 | 8/2008 | Krivoruchko |
| 7,479,153 B2 | 1/2009 | Belef |
| 7,494,497 B2 | 2/2009 | Weber |
| 7,517,352 B2 | 4/2009 | Evans |
| 7,632,288 B2 | 12/2009 | Wu |
| 7,637,885 B2 | 12/2009 | Maschke |
| 7,648,502 B2 | 1/2010 | Jacques |
| 7,658,744 B2 | 2/2010 | Jackson |
| 7,662,163 B2 | 2/2010 | Grayzel |
| 7,691,116 B2 | 4/2010 | Goodin |
| 7,734,332 B2 | 6/2010 | Sher |
| 7,736,375 B2 | 6/2010 | Crow |
| 7,753,907 B2 | 7/2010 | Dimatteo |
| 7,754,047 B2 | 7/2010 | Kelley |
| 7,758,604 B2 | 7/2010 | Wu |
| 7,771,447 B2 | 8/2010 | Kunis |
| 7,780,626 B2 | 8/2010 | Wu |
| 7,799,043 B2 | 9/2010 | O'Brien |
| 7,833,223 B2 | 11/2010 | Vakharia |
| 7,862,575 B2 | 1/2011 | Tal |
| 7,883,537 B2 | 2/2011 | Grayzel |
| 7,887,557 B2 | 2/2011 | Kelley |
| 7,901,378 B2 | 3/2011 | Solar |
| 7,919,910 B2 | 4/2011 | Eidenschink |
| 7,955,350 B2 | 6/2011 | Konstantino |
| 7,985,234 B2 | 7/2011 | Wang |
| 8,070,729 B2 | 12/2011 | Solar |
| 8,080,026 B2 | 12/2011 | Konstantino |
| 8,348,987 B2 | 1/2013 | Eaton |
| 2003/0055444 A1 | 3/2003 | Evans |
| 2003/0163148 A1 | 8/2003 | Wang |
| 2003/0195546 A1 | 10/2003 | Solar |
| 2003/0208219 A1 | 11/2003 | Aznoian |
| 2004/0087876 A1 | 5/2004 | Eskuri |
| 2004/0122458 A1 | 6/2004 | Opie |
| 2004/0133148 A1 | 7/2004 | Jacques |
| 2004/0193196 A1 | 9/2004 | Appling et al. |
| 2004/0199088 A1 | 10/2004 | Bakos |
| 2005/0085836 A1 | 4/2005 | Raymond |
| 2005/0119678 A1 | 6/2005 | O'Brien |
| 2005/0137615 A1 | 6/2005 | Mapes |
| 2005/0197593 A1 | 9/2005 | Burbank |
| 2005/0209617 A1 | 9/2005 | Koven |
| 2005/0240148 A1 | 10/2005 | Cheves |
| 2005/0288629 A1 | 12/2005 | Kunis |
| 2006/0085026 A1 | 4/2006 | Appling et al. |
| 2006/0111736 A1 | 5/2006 | Kelley |
| 2006/0116700 A1 | 6/2006 | Crow |
| 2006/0116701 A1 | 6/2006 | Crow |
| 2006/0178685 A1 | 8/2006 | Melsheimer |
| 2006/0206125 A1 | 9/2006 | Fogarty |
| 2007/0016232 A1 | 1/2007 | St. Martin |
| 2007/0233163 A1 | 10/2007 | Bombard |
| 2007/0250096 A1 | 10/2007 | Yamane |
| 2007/0270893 A1 | 11/2007 | Pikus |
| 2008/0045987 A1 | 2/2008 | Lee |
| 2008/0077164 A1 | 3/2008 | Murphy |
| 2008/0077165 A1 | 3/2008 | Murphy |
| 2008/0147103 A1 | 6/2008 | Shekalim |
| 2008/0215077 A1 | 9/2008 | Sepetka |
| 2008/0228208 A1 | 9/2008 | Wulfman |
| 2008/0249552 A1 | 10/2008 | Eliachar |
| 2008/0255595 A1 | 10/2008 | Buchbinder |
| 2008/0255596 A1 | 10/2008 | Jenson |
| 2008/0269789 A1 | 10/2008 | Eli |
| 2008/0306499 A1 | 12/2008 | Katoh |
| 2009/0012548 A1 | 1/2009 | Thatcher |
| 2009/0099581 A1 | 4/2009 | Kim |
| 2009/0105686 A1 | 4/2009 | Snow |
| 2009/0125044 A1 | 5/2009 | Lary |
| 2009/0306582 A1 | 12/2009 | Granada |
| 2010/0010521 A1 | 1/2010 | Kurrus |
| 2010/0023035 A1 | 1/2010 | Kontos |
| 2010/0057077 A1 | 3/2010 | Ducharme |
| 2010/0094259 A1 | 4/2010 | Makower |
| 2010/0094320 A1 | 4/2010 | Arat |
| 2010/0121361 A1 | 5/2010 | Plowe |
| 2010/0125266 A1 | 5/2010 | Deem |
| 2010/0137893 A1 | 6/2010 | Kilemnick |
| 2010/0198191 A1 | 8/2010 | Clifford |
| 2010/0234864 A1 | 9/2010 | Keller |
| 2010/0286720 A1 | 11/2010 | Shaked |
| 2011/0034949 A1 | 2/2011 | Solar |
| 2011/0071559 A1 | 3/2011 | Holman |

(56) References Cited

U.S. PATENT DOCUMENTS

| | | |
|---|---|---|
| 2011/0087257 A1 | 4/2011 | To |
| 2011/0118774 A1 | 5/2011 | Solar |
| 2011/0125132 A1 | 5/2011 | Krolik et al. |
| 2011/0125172 A1 | 5/2011 | Gelbart |
| 2011/0160645 A1 | 6/2011 | Sutermeister et al. |

FOREIGN PATENT DOCUMENTS

| | | |
|---|---|---|
| WO | WO-2010/002549 | 1/2010 |
| WO | WO-2010/003135 | 1/2010 |
| WO | WO-2010/011956 | 1/2010 |

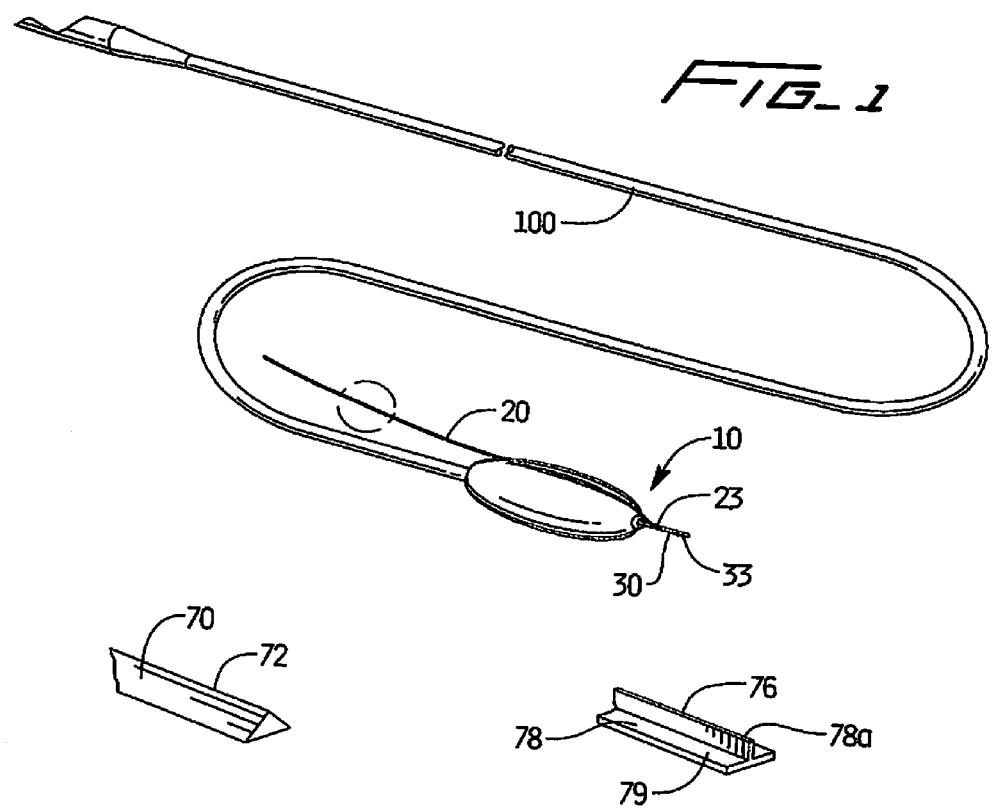
FIG_1
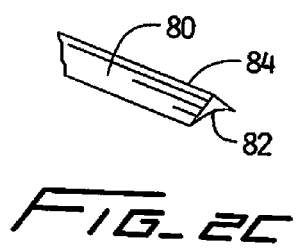
FIG_2A  FIG_2B
FIG_2C
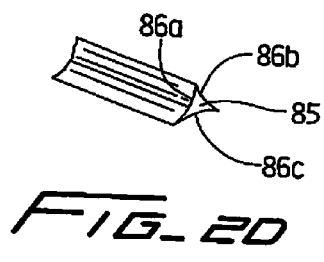 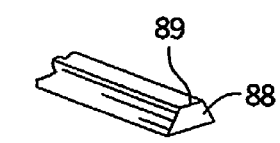
FIG_2D  FIG_2E

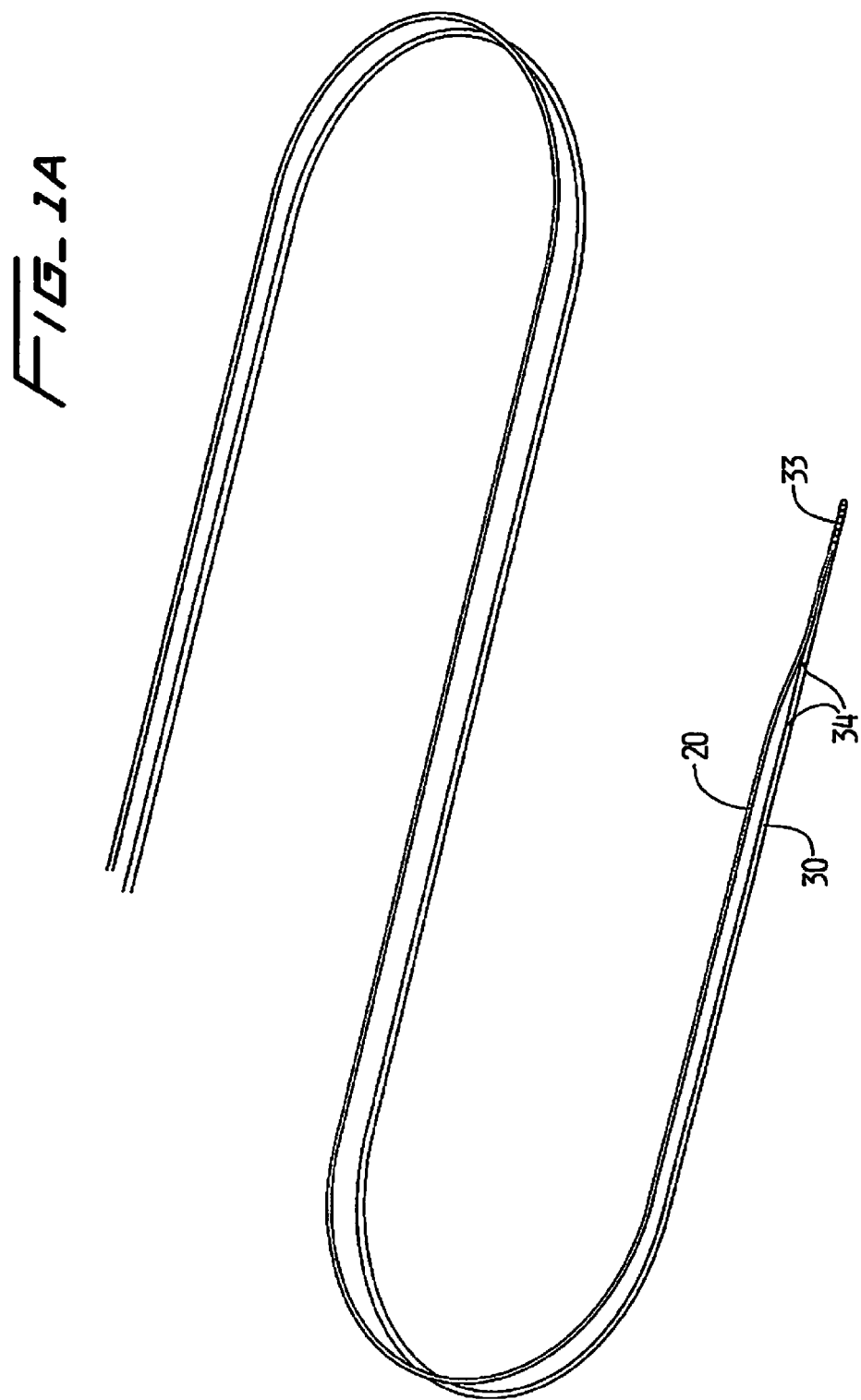

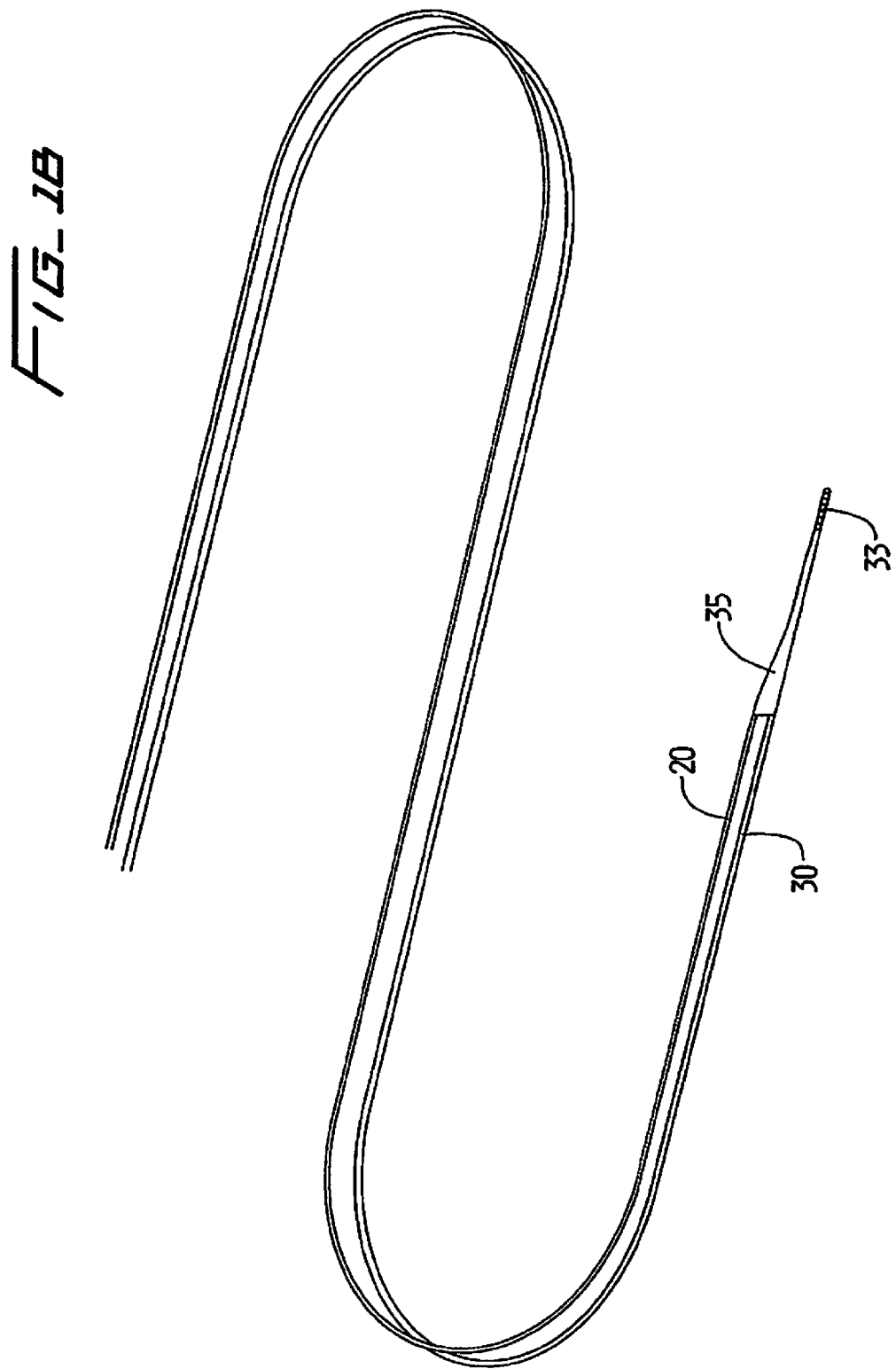

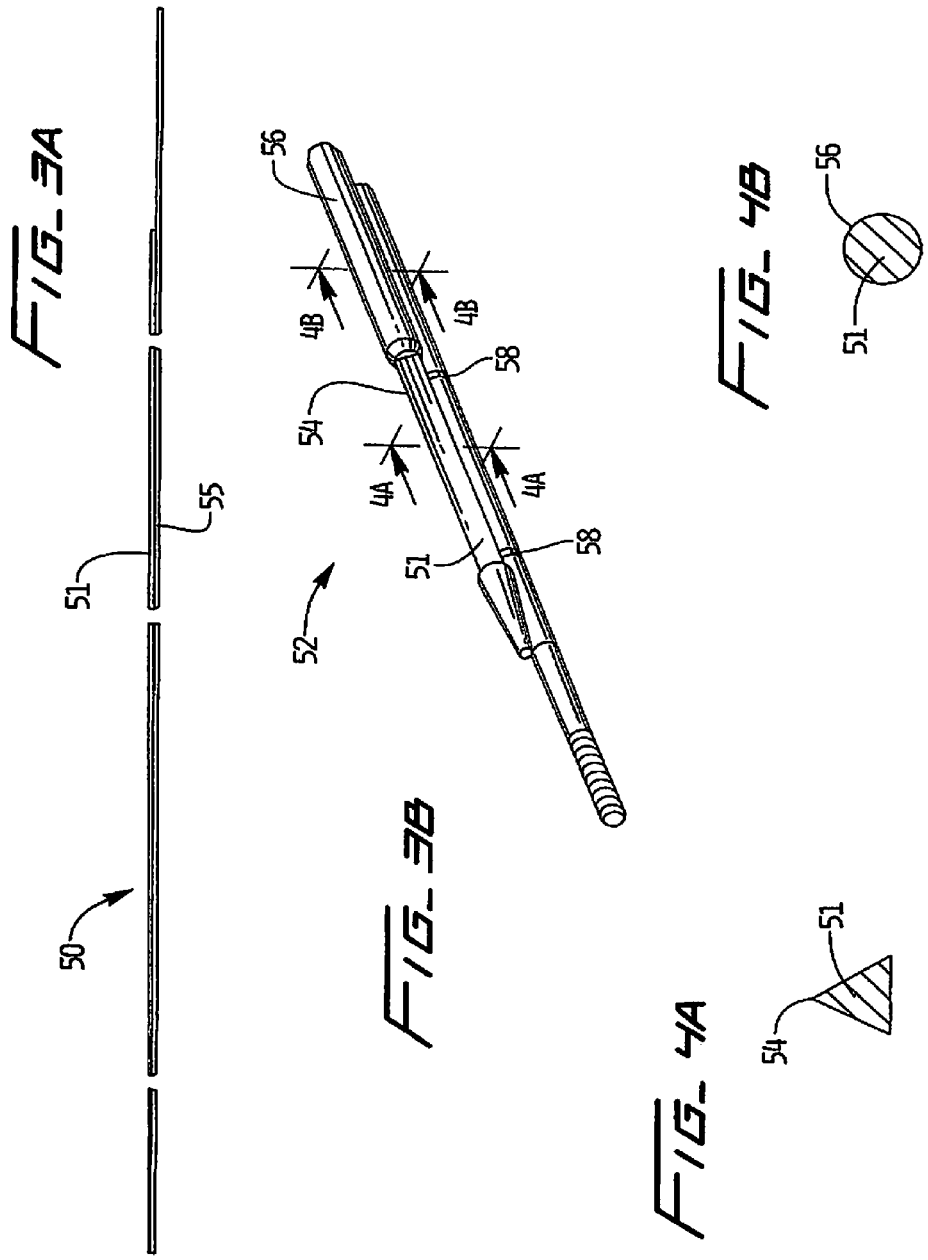

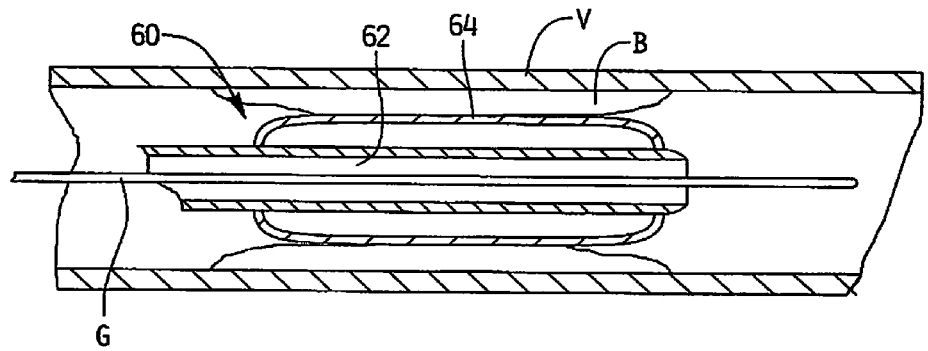
FIG_5
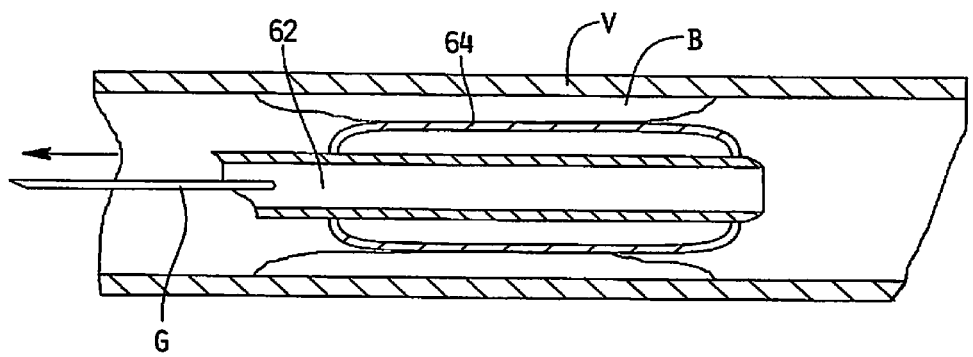
FIG_5A
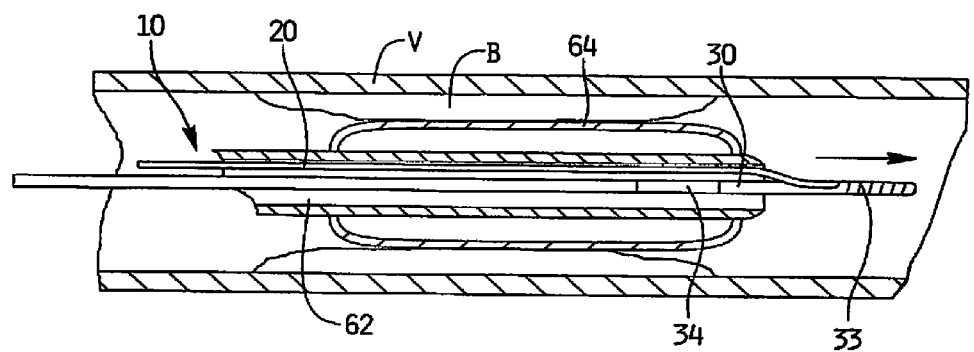
FIG_5B

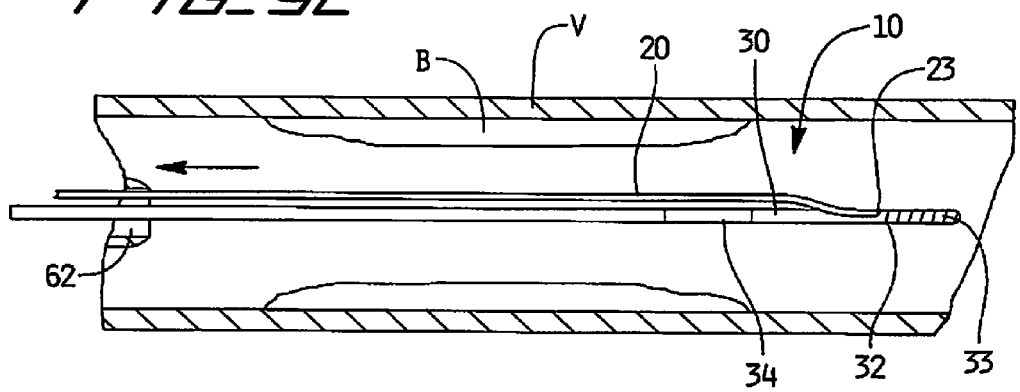
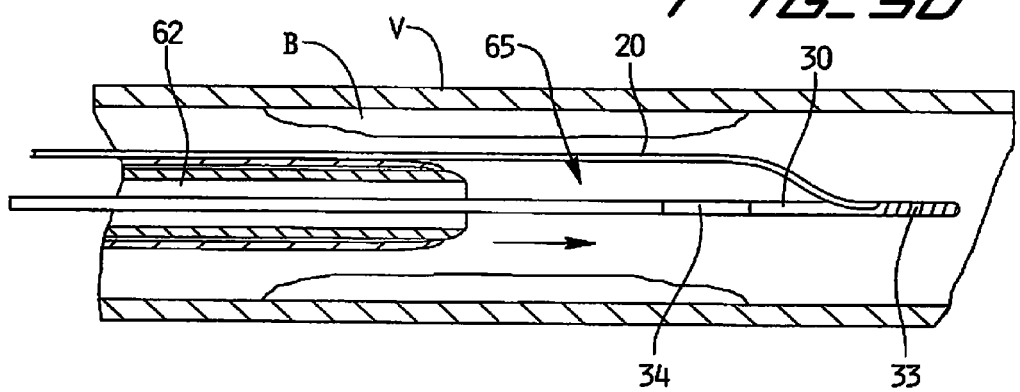
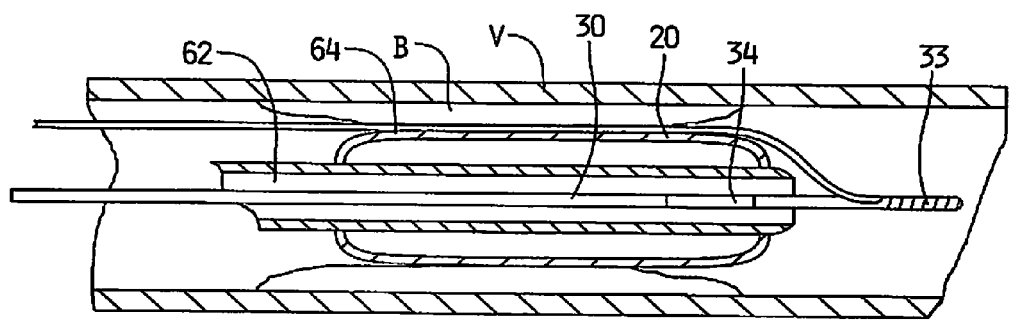

CUTTING WIRE ASSEMBLY FOR USE WITH A CATHETER

This application is a continuation of co-pending U.S. application Ser. No. 14/176,128, filed Feb. 9, 2014, which is a divisional of U.S. application Ser. No. 13/226,735, filed Sep. 7, 2011, now U.S. Pat. No. 8,685,050, which claims priority from provisional application Ser. No. 61/390,217, filed Oct. 6, 2010. The entire contents of each of these applications are incorporated herein by reference.

BACKGROUND

Technical Field

This application relates to a system and method for treating stenotic lesions of a vessel and more particularly relates to a cutting wire for use with a catheter to open stenotic lesions in vessels.

Background of Related Art

Several methods have been utilized to treat stenotic lesions of vessels. With stenotic lesions, the vessel diameter is constricted and therefore attempts have been made to widen this constriction. One method is an invasive surgical procedure where the vessel wall is cut open and the portion containing the plaque or other constricting structure is removed. This procedure is traumatic, complex, and results in a long recovery time for the patient. It also causes a weakening of the vessel wall since a portion of the wall is removed. A weakened wall can ultimately result in an aneurysm which is a dilatation (expansion) of the artery, which adversely affects vessel function and if not surgically treated could be life threatening to the patient.

In order to reduce trauma to the patient, reduce the patient recovery time and reduce hospital costs, minimally invasive procedures have been developed to treat stenotic lesions. Balloon angioplasty is one such method. In angioplasty, a balloon is placed in the stenosed (restricted) portion of the vessel and inflated to compress the plaque against the vessel wall, thereby increasing the lumen in the vessel to improve blood flow. That is, the balloon is inflated to push the lesion radially outwardly to widen the passageway. Some stenotic lesions are resistant to conventional pressure balloons. Consequently, high pressure balloons have been developed to treat resistant stenotic lesions. However, such high pressure balloons apply more force and increase the risk of vessel trauma and rupture. Moreover, sometimes lesions are even resistant to these high pressure balloons.

Additionally, the use of these angioplasty balloon catheters oftentimes have only short term effect as it has been found that restensois frequently occurs after such treatment.

In an attempt to address such drawbacks as reducing the likelihood of restenosis and trauma, as well as to treat vessels with highly resistant lesions, cutting balloon catheters were developed. One such device is disclosed for example in U.S. Pat. No. 5,196,024 which describes a catheter with a balloon and longitudinal cutting edges. One of the many disadvantages of this device, however, is it requires modifications of balloon catheters which significantly increases the cost of the catheter. Another disadvantage is that instead of using the procedural catheter, a different catheter may be required with a cutting balloon. Consequently, the surgeon would need to decide prior to the procedure which type of catheter to utilize, although this may not always be practical as the information to determine the type (e.g. resistance) of the lesion may not be available until the lesion is accessed and the extent of the disease is known. Thus, for example, the surgeon may insert an angioplasty catheter, inflate the balloon and find that it is insufficient to widen the vessel passageway. The surgeon would then need to conduct the time consuming task of removing the catheter and inserting a cutting balloon catheter, threading it through the vascular system over a guidewire. Since the catheters are inserted from a remote site, e.g. through the femoral artery, these catheter exchanges take time and increase trauma to the patient. Additionally, it adds to the cost of the procedure since two catheters would be required. In order to properly treat the diverse size and condition of each lesion a large inventory of multiple sized cutting balloons would be required.

Conversely, in certain procedures, utilizing a cutting balloon in soft lesions increases the risk of trauma or damage to the vessel and therefore it would not be desirable to use a cutting balloon catheter. Thus, an exchange for an angioplasty catheter would be necessary.

Such catheter exchanges might also require guidewire exchanges since the standard 0.035" guidewire utilized for an angioplasty catheter may be too large for the 0.018" cutting balloon catheter. The guidewire exchanges complicate the procedure, increase the risk to the patient and increase the procedure time, thereby increasing costs to the patient.

U.S. Pat. No. 7,131,981 attempts to address the foregoing issues by providing a conversion device comprising an insertion tube insertable into the normal 0.035" guidewire lumen of an angioplasty catheter. This device would not work for angioplasty catheters with small guidewire lumens. The tube has two jacket segments and a guide insert device having a channel and four guide channels. Because of the complexity of the device, the cutting elements in the four channels would need to be sufficiently thin to be maintained in the smaller diameter device. Such thin (small diameter) cutting elements however may be too flexible and not have adequate stiffness to be effective. Additionally, the cutting elements are attached at one end, having an opposite free end which can potentially damage and perforate the vessel wall during use.

The need therefore exists for an improved, more simplified device and method to enable the selective use of a cutting wire for treating stenosis.

SUMMARY

The present invention overcomes the disadvantages and deficiencies of the prior art.

In one aspect, the present invention provides a method of treating a lesion in a body lumen comprising inserting a cutting member and tracking member through a first lumen of a catheter, withdrawing the catheter from the cutting member and tracking member, inserting the catheter over the tracking member while leaving the cutting member outside the catheter, and expanding a portion of the catheter to move the cutting member into cutting contact with the lesion to enlarge a passageway in the body lumen.

In some embodiments, the step of inserting a catheter over the tracking member comprises reinserting the same catheter through which the cutting member and tracking member were initially inserted. In other embodiments, a different catheter is utilized.

The catheter preferably includes an expandable balloon, and the step of expanding the catheter preferably includes the step of expanding a portion of the balloon to cause the cutting member to be moved radially with respect to the catheter. Preferably, the step of expanding a portion of the catheter causes a gap between the cutting member and tracking member to widen.

In some embodiments, the cutting member has a cutting edge opposite an edge facing the tracking member, and expansion of a portion of the catheter forces the cutting edge into a diseased narrowed section within the lesion.

In preferred embodiments, the cutting member and tracking member are attached at their distal ends and inserted as a unit through the lumen of the catheter.

In some embodiments, the length of the tracking member can exceed the length of the cutting member. In some embodiments the cutting member has a first portion of a first configuration and a second portion of a second configuration, the second portion including a cutting surface and the first portion being atraumatic. In some embodiments, a height of the second portion is less than a height of the first portion.

In some embodiments, marker bands are provided on the tracking member. The tracking member can have a coil at a distal tip.

In another aspect, the present invention provides a method of treating a lesion in a body lumen to enlarge a passageway in the body lumen comprising inserting a cutting member and tracking member into the vessel, inserting a catheter over the tracking member so the tracking member extends through a first lumen of the catheter and the cutting member does not extend through, e.g. remains outside, the first lumen, and moving the cutting member away from the tracking member into cutting contact with the lesion to enlarge the passageway in the body lumen.

Preferably, the step of inserting a cutting member and tracking member comprises the step of inserting the cutting member and tracking member through a lumen of a catheter.

In some embodiments, the catheter through which the cutting and tracking members are initially inserted is the same catheter subsequently inserted over the tracking member. In other embodiments, a different catheter is utilized. In some embodiments, the step of moving the cutting member comprises the step of expanding a balloon of the catheter. In preferred embodiments, the cutting member and tracking member are wires and are attached at their distal end and inserted as a unit into the vessel.

In some embodiments, the tracking member has a coil tip. A heat shrink can be provided over an attachment region of the cutting and tracking members.

In some embodiments, the cutting member is substantially circular in cross-section in a proximal region and substantially triangular cross-section in a distal region.

In another aspect, the present invention provides a device for treating a lesion in a body lumen to enlarge a passageway in a body lumen comprising a cutting member having a proximal portion and a distal portion and a tracking member having a proximal portion and a distal portion. The cutting member and tracking member are connected at their distal portions and insertable into the body lumen as a unit, the cutting member configured for movement in a direction transverse to a longitudinal axis of the tracking member to widen a gap between the cutting member and tracking member at least at a distal region.

In some embodiments, the cutting member has a cutting surface on a first surface opposite a second surface facing the tracking member. In some embodiments, the cutting member has a cutting surface with a flat edge on an edge opposite a surface facing the tracking member. In some embodiments, the second surface has a convex surface. The tracking member can include a plurality of marker bands.

In another aspect, the present invention provides a system for treating lesions in a body lumen to enlarge a restriction in the body lumen comprising a catheter having a lumen and an expandable portion and a cutting assembly including a cutting member and tracking member, the tracking member attached to the cutting member. The expandable portion of the catheter is expandable to move the cutting member in a direction transverse to a longitudinal axis of the tracking member, the cutting member having a cutting surface configured to treat the lesion to enlarge a passageway in the body lumen when moved by the expandable portion of the catheter.

In some embodiments, the cutting member and tracking member are connected at distal regions thereof. The tracking member can include a plurality of marker bands. The cutting member in some embodiments is substantially circular in cross-section in a proximal region and substantially triangular in a distal region. In preferred embodiments, the expandable portion of the catheter comprises an inflatable balloon. The tracking member can have a coil at a distal end and a heat shrink can be positioned over the attachment region of the cutting and tracking members.

BRIEF DESCRIPTION OF THE DRAWINGS

Preferred embodiment(s) of the present invention are described herein with reference to the drawings wherein:

FIG. 1 is a perspective view of a conventional balloon catheter and a first embodiment of the cutting wire assembly (unit) of the present invention and showing the balloon expanded;

FIG. 1A is a perspective view of the cutting assembly of FIG. 1;

FIG. 1B is a perspective view similar to FIG. 1A showing the shrink wrap over a distal portion;

FIG. 2A is an enlarged perspective view of the area of detail of FIG. 1 showing a portion of the cutting wire in accordance with one embodiment;

FIG. 2B is a perspective view similar to FIG. 2A showing another embodiment of the cutting wire;

FIG. 2C is a perspective view similar to FIG. 2A showing yet another embodiment of the cutting wire;

FIG. 2D is a perspective view similar to FIG. 2A showing another embodiment of the cutting wire;

FIG. 2E is a perspective view similar to FIG. 2A of yet another embodiment of the cutting wire;

FIG. 3A is a perspective view of another embodiment of the cutting wire assembly;

FIG. 3B is a close up perspective view of a distal portion of the cutting assembly of FIG. 3A.

FIG. 4A is a cross-sectional view of the cutting wire taken along line 4A-4A of FIG. 3B;

FIG. 4B is a cross-sectional view of the cutting wire taken along line 4B-4B of FIG. 3B;

FIGS. 5-5E illustrate the method steps for use of the cutting wire assembly of the present invention, the drawings showing cross-sectional views, wherein FIG. 5 illustrates a conventional balloon catheter inserted over a conventional guidewire;

FIG. 5A illustrates withdrawal of the conventional guidewire;

FIG. 5B illustrates insertion of the cutting and tracking members of the present invention through the balloon catheter lumen;

FIG. 5C illustrates withdrawal of the balloon catheter leaving the cutting and tracking members within the vessel lumen;

FIG. 5D illustrates the balloon catheter inserted over the tracking member; and

FIG. 5E illustrates expansion of the balloon of the balloon catheter to force the cutting wire into cutting contact with the lesion.

DETAILED DESCRIPTION OF PREFERRED EMBODIMENTS

Referring now in detail to the drawings wherein like reference numerals identify similar or like components throughout the several views, the cutting assembly of the present invention includes a cutting member (or element) and a tracking member (or element). More, specifically, cutting assembly includes an assembly 10 having a tracking member, designated generally by reference numeral 30 and preferably in the form of a wire, and a cutting member, designated generally by reference numeral 20 and preferably in the form of a wire. As discussed in more detail below, the tracking wire 30 and cutting wire 20 are preferably attached at a distal portion so they are insertable as a unit. The wire assembly 10, as described below, can be used with a conventional catheter, such as an angioplasty catheter.

The device of the present invention functions to treat the stenotic lesion inside the vessel wall, thereby opening or enlarging the passageway in the vessel which was restricted. The stenosis can be a result of plaque buildup, endothelial growth, blood clots, etc. The device can also be used to treat other lesions restricting passageways in other body lumens.

With reference to FIGS. 1 and 5C, cutting member in the form of a wire 20 has a distal portion 23 which is connected to a distal portion 32 of a tracking member in the form of a wire 30. In the illustrated embodiment, a distalmost tip 23 of the cutting wire 20 is attached to the tracking or guidewire 30. One way of attachment is to twist the wires together. Other methods of attachment are also contemplated such as welding, bonding or placement of a separate element such as a collar over the end of the wires to frictionally engage the wires. The cutting wire 20 remains unattached proximal of the distal connection (attachment) region to enable it to be separated from the tracking wire 30 e.g. moved transversely with respect to the longitudinal axis of the tracking wire 30. In FIG. 5C, the initial position of the wires 20, 30 are shown; in FIGS. 5D and 5E the wires 20, 30 are further separated as described in detail below.

Tracking member has a coil tip 33 for flexibility. A heat shrink wrap 35 can be placed over the connection region of the cutting wire 20 and a tracking wire 30. Marker bands 34 can be provided for imaging.

Note the tracking wire and cutting wire can be of substantially the same length, both extending out of the body for reinsertion of a catheter over the tracking wire as described below. Alternatively, they can be of different lengths. The cutting member (wire) has a proximal portion and a distal portion, the proximal portion configured to extend outside the patient when the cutting member is positioned in the body lumen adjacent the lesion.

Various configurations of the cutting wire 20 are illustrated to effectively treat lesions. In the embodiment of FIG. 2A, the wire 70 is substantially triangular in cross section forming a V-shaped cutting surface 72 on a first surface opposite a second surface facing the tracking wire 30. In the embodiment of FIG. 2B, a cutting edge 76 on first surface 78a of cutting wire 78 with a substantially planar outer edge extends from the substantially planar base 79. In FIG. 2C, a surface 82 of the wire 80 opposite the cutting surface 84 and facing the tracking wire 30 is convex. This surface 82 can conform to the outer surface of the catheter balloon. Two or alternatively three sides of the cutting wire can be convex as in sides 86a, 86b, 86c of wire 85 of FIG. 2D. In the embodiment of FIG. 2E, wire 88 is trapezoidal in cross section with a cutting surface 89 on the outer surface. Other shapes are also contemplated, including but not limited to polygonal shapes that are substantially: square, rectangular, rhombus, hexagonal, pentagonal, octagonal, diamond shaped, etc. A round or oval wire cross-section with a sharpened surface is also contemplated. Caltrop shapes and upside down T-shapes are also contemplated.

Note, if desired, only a portion of the cutting wire (member) can have the cutting edge or surface, e.g. the distal region, with a remaining portion being atraumatic and non-cutting. This is shown for example in the embodiment of FIGS. 3A and 3B where wire 51 of cutting assembly 50 has a distal portion having a cutting edge 54. (Although shown as a substantially triangular cross-section, other cross-sectional shapes are also contemplated including those discussed above). Proximal of distal portion 52, the portion 56 is atraumatic and can be substantially circular in cross-section as shown in FIG. 4B. (Other shapes are also contemplated). The distal region of wire 51 can be conical and can have an atraumatic surface. Note the height of the cutting surface region can be less than the height (e.g. diameter) of the atraumatic portion 56.

A coil such as coil 33, can be provided at the distal tip of tracking member (wire) 55. Several marker bands 58 are provided on tracking wire 55 for imaging. A heat shrink wrap such as shrink wrap 35 of FIG. 1B which covers the distal and connecting region of wires 20 and 30 can be provided over the distal tip and connection region of the cutting and tracking wires 51, 55 of FIG. 3B.

One method of use of the wire assembly 10 of the present invention will now be described. The method is described for using wire assembly 10, but it should be appreciated that the same method can be used for wire assembly 50 (and for the other cutting wire configurations). Initially, a conventional catheter 100, such as conventional angioplasty catheter, is inserted over a conventional guidewire G to the treatment site as shown in FIG. 5. Guidewire G extends through a lumen 62 in the catheter 60. Access to the vessel can be obtained through the femoral artery or vein for example. Note the proximal end of the catheter 60 and guidewire G extend outside the patient's body. The angioplasty catheter 60 has an inflatable balloon 64 which is in fluid communication with an inflation lumen of the catheter as is conventional. At the target site, inflation of the balloon 64 expands the balloon 64 to expand the lesion B and widen the lumen of the vessel V.

If the stenotic lesion cannot be successfully opened by a conventional balloon due to lack of force, the wire assembly 10 (or assembly 50) of the present invention can be utilized. In this case, the guidewire G is removed from the guidewire lumen 62 of the catheter 60 (see FIG. 5A) and the wire assembly 10 (or 50) is inserted through the lumen 62 as shown in FIG. 5B. Thus, by insertion through the lumen 62, the tracking guidewire 30 (or 55) and cutting wire 20 (or 51) of wire assembly 10 (or 50) are inserted to the target site.

Next, the catheter 60 is removed from the treatment site and vessel, and removed from the body, leaving the wire assembly 10 at the target site as shown in FIG. 5C. The catheter 60 is then reinserted over proximal end of tracking wire 30. Note that instead of reinserting the same catheter used in the step of FIG. 5, alternatively, a different balloon catheter (or catheter with other expandable member) can be inserted. In either event, the catheter is inserted over the proximal portion of the tracking wire 30 such that the tracking wire 30 extends through the lumen 62; however, cutting wire 20 remains outside the lumen 62 and thus does not extend through lumen 62 as shown in FIG. 5D. In this manner, the tracking wire 30 provides a guide for the catheter 60 to the target site, while the cutting wire 20 remains adjacent an outer surface of the catheter 60 for subsequent expansion into contact with the lesion. As shown in FIG. 5D, there is an increased gap 65 between the cutting wire 20 and tracking wire 30 caused by the catheter 60 positioned between the two wires 20, 30.

To expand or move the wire 20 transversely with respect to the longitudinal axis of the tracking wire 30 (and transverse to the longitudinal axis of the catheter 60), the balloon 64 is inflated, forcing the cutting wire 20 radially and into contact with the lesion B so the cutting edge or surface can treat the lesion. It should be appreciated that instead of a balloon, a mechanical expander or other structure can be used to force the cutting wire 20 into contact with the lesion. If desired, the balloon 64 can be deflated and the wire assembly easily rotated to another position for subsequent transverse movement by the cutting wire into contact with another region of the lesion B. In this manner, the select portions of the stenosis can be treated, as the cutting wire 20 is expanding in one direction. The cutting wire assembly 50 can be used in a similar manner.

As can be appreciated, the method described above utilizes the same catheter for the initial step (FIG. 5) as well as for the subsequent step of reinsertion for placement only over the tracking wire 30 (FIG. 5D). However, it is also contemplated that a different catheter can be used for insertion over tracking wire 30 in the step of FIG. 5D.

As can be appreciated, the wire assembly 10 can accommodate balloon catheters having relatively small guidewire lumens.

Also, although access is described through the femoral artery, other approaches to the target site are also contemplated. Additionally, although described for use to treat lesions in vessel lumens, it can also be used to remove other structures constricting the passageway in the vessel or in other body lumens.

The cutting and tracking components are illustrated as wires, but other structures for the cutting member and tracking member are also contemplated such as a hard plastic cut tube or a metal hypotube. The metal hypotube can be formed with a cutting surface or alternatively have a cutting member such as a cutting tube attached thereto.

The cutting wire assembly of the present invention as described can be used in various vessels including for example, veins such as the femoral veins, grafts such as dialysis grafts, etc. Other vessels are also contemplated such as use in carotid arteries, coronary arteries, the descending aorta and renal arteries, the external iliac and internal iliac arteries and the common femoral and deep femoral arteries. Applications for this device include, but are not limited to, treating stenotic venous and arterial anastomosis, lesions resistant to conventional angioplasty, stent restenosis, and vessels with buildup of intima, etc.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A system for treating a lesion in a body lumen of a patient to enlarge a passageway in the body lumen comprising:
   a catheter having a lumen and an expandable portion; and
   a cutting assembly including a cutting member and a tracking member, the tracking member attached to the cutting member, wherein the expandable portion of the catheter is expandable to move the cutting member in a direction transverse to a longitudinal axis of the tracking member, the cutting member having a proximal portion and a distal portion, the proximal portion configured to extend outside the patient when the cutting member is positioned in the body lumen adjacent the lesion, the cutting member having a cutting surface configured to treat the lesion to enlarge the passageway in the body lumen when moved by the expandable portion of the catheter.

2. The system of claim 1, wherein the cutting member and tracking member are connected at distal regions thereof.

3. The system of claim 2, wherein the expandable portion comprises an inflatable balloon.

4. The device of claim 1, wherein the tracking member has a coil at a distal end, and a heat shrink is positioned over an attachment region of the cutting member and tracking member.

5. The device of claim 1, wherein the tracking member includes a plurality of marker bands.

6. The system of claim 1, wherein the cutting member at a cutting region is substantially triangular in cross-section.

7. The system of claim 6, wherein the cutting member is circular in region proximal of the cutting region.

8. The system of claim 1, wherein the cutting member has a first portion of a first configuration and a second portion of a second configuration, the second portion including a cutting surface and the first portion being atraumatic.

9. The system of claim 8, wherein a height of the first portion is less than a height of the second portion.

10. The system of claim 1, wherein the cutting member has a second surface opposite the cutting surface facing the tracking member.

11. The system of claim 1, wherein the cutting member is a wire.

12. The system of claim 11, wherein the tracking member is a wire.

13. The system of claim 1, wherein the tracking member is a wire.

14. The system of claim 1, wherein the cutting member has a proximal region of greater height than a distal region.

* * * * *